US00PP11252P

United States Patent [19]

Tyssowski

[11] Patent Number: Plant 11,252

[45] Date of Patent: Feb. 29, 2000

[54] ***GERANIUM MACULATUM* PLANT NAMED 'ELIZABETH ANN'**

[75] Inventor: Carol Tyssowski, Baltimore, Md.

[73] Assignee: Leslie Grayson, Royersford, Pa.

[21] Appl. No.: 09/004,122

[22] Filed: Jan. 7, 1998

[51] Int. Cl.[7] ..... A01H 5/00

[52] U.S. Cl. ..... Plt./324

[58] Field of Search ..... Plt./324

*Primary Examiner*—Howard J. Locker
*Assistant Examiner*—Kent L. Bell
*Attorney, Agent, or Firm*—C. A. Whealy

[57] ABSTRACT

A new and distinct cultivar of *Geranium maculatum* plant named 'Elizabeth Ann', characterized by its vigorous growth rate; upright and freely branching plant habit; brownish red stem color; unique chocolate brown leaf color; numerous single lavender flowers; and brown peduncles and pedicels.

2 Drawing Sheets

The present invention relates to a new and distinct cultivar of Hardy Geranium plant, botanically known as *Geranium maculatum*, and hereinafter referred to by the cultivar name 'Elizabeth Ann'.

The new cultivar was discovered and selected by the inventor from seedling progeny from a cross of unidentified selections of *Geranium maculatum* in an outdoor production area in Baltimore, Md.

Asexual reproduction of the new cultivar by divisions taken at Baltimore, Md., and Royersford, Pa., has shown that the unique features of this new Hardy Geranium are stable and reproduced true to type in successive generations.

The following traits have been repeatedly observed and are determined to be the unique characteristics of 'Elizabeth Ann'. These characteristics in combination distinguish 'Elizabeth Ann' as a new and distinct cultivar:

1. Vigorous growth rate, upright plant habit, freely branching.
2. Brownish red stem color.
3. Unique chocolate brown leaf color. During the spring and summer, foliage maintains brown coloration in partial sun and full sun exposures. Foliage turns reddish brown in autumn. Petioles, brown.
4. Numerous single lavender flowers. Plants flower throughout spring until summer and may reflower in the autumn.
5. Brown peduncle and pedicel color.
6. Plants usually do not become dormant during the winter.

The cultivar 'Elizabeth Ann' has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical plant of 'Elizabeth Ann'.

The photograph at the top of the second sheet comprises a close-up view of a typical flowers of 'Elizabeth Ann'.

The photograph at the bottom of the second sheet comprises a close-up view of typical leaves of 'Elizabeth Ann'. Foliage and flower colors in the photographs may appear different from the actual colors due to light reflectance.

DETAILED BOTANICAL DESCRIPTION

The following observations, measurements and comparisons describe plants grown in Royersford, Pa., under conditions which approximate commercial field practice during the spring. In the following description, color references are made to The Royal Horticultural Society Colour Chart except where general terms of ordinary dictionary significance are used.

Classification:
- *Botanical.*—*Geranium maculatum* cv. 'Elizabeth Ann'.
- *Commercial.*—Hardy Geranium.

Parentage:
- *Male parent.*—Unidentified selection of *Geranium maculatum.*
- *Female parent.*—Unidentified selection of *Geranium maculatum.*

Propagation:
- *Type.*—By divisions.
- *Time to initiate and develop roots.*—About 14 days at 24° C.
- *Rooting habit.*—Thick and freely branching.

Plant description:
- *General appearance.*—Upright growth habit, inverted triangle. Appropriate for 15-cm containers.
- *Growth rate.*—Rapid, vigorous.
- *Plant height.*—About 48 cm.
- *Plant width.*—About 32 cm.
- *Branching habit.*—Freely, mostly basally branching. Usually about 8 to 10 lateral branches per plant. Pinching, or removal of the terminal apex, is not required.
- *Lateral branch length.*—About 25 cm.
- *Internode length.*—About 1.5 cm.
- *Stem color.*—199A with hints of 183A.
- *Foliage description.*—Arrangement: Opposite or single. Shape: Generally palmate, deeply lobed. Apex: Acuminate. Base: Hastate. Length: About 5 cm. Width: About 10 cm. Texture: Slightly pubescent on upper surface. Margin: Incised, deeply lobed. Color: Young and fully expanded leaves, upper surface: 200A. Young and fully expanded leaves, lower surface: 200D. Venation, upper surface: 144B. Venation, lower surface: 144C. Petiole: Length: About 5 cm. Diameter: About 2 mm. Color: 177A. Durability to rain, wind and stress conditions: Moderate.

Flowering Description:

*Flowering habit.*—Single, upright flowers arranged in umbels with 4 to 12 flowers per umbel.

*Natural flowering season.*—Recurrent, spring until summer. Plants may reflower in the autumn.

*Flower longevity.*—Flowers last about 5 days on the plant. Flowers self-cleaning.

*Flowers borne.*—Flower buds develop in apical leaf axils. Umbels are displayed above the foliage. Flowers face outward to upward.

*Umbel diameter.*—About 7 cm.

*Umbel depth (height).*—About 5 cm.

*Flowers.*—Shape: Rounded, 5 — petaled. Diameter: About 3.5 cm. Depth (height): About 7 mm.

*Petals.*—Shape: Obovate with obtuse apex and cuneate base. Aspect: Flat. Length: About 1.8 cm. Width: About 1.5 cm. Texture: Smooth. Margin: Entire. Color: Opening flower, upper surface: 87C. Opening flower, lower surface: 84B. Opened flower, upper surface: 88D, becoming darker, 93C, with subsequent development fading to near white at the point of petal attachment, giving an overall appearance of a whitish eye in the fully opened flower. Opened flower, lower surface: 85A. Peduncle (umbel stem): Angle: Erect to 25° to vertical axis. Texture: Slightly pubescent. Color: 177A.

*Pedicel (individual flower stem).*—Angle: About 25° to vertical axis. Length: About 8.5 mm. Texture: Slightly pubescent. Color: 174B.

*Flower bud.*—Shape: Elliptical. Length: About 7 mm. Diameter: About 4 mm. Color: 144A.

*Sepals.*—Shape: Elliptical with acute apex. Arrangement: Rosette. Quantity: 5. Length: About 1 cm. Width: About 4 mm. Texture: Pubescent. Margin: Entire. Color: Upper surface: 144B. Lower surface: 144A.

*Reproductive organs.*—Androecium: Stamen number: Ten. Anther size: About 1.5 mm. Anther color: 8C. Pollen color: 7B, moderate. Gynoecium: Pistil number: 1. Pistil length: About 1 cm. Stigma shape: Five stigmatic whorled branches. Stigma color: 16A. Style length: About 5 mm. Style color: 151B.

*Seed.*—Shape: Oval. Length: About 3 mm. Diameter: About 2 mm. Color: 200C.

Disease resistance: No fungal, bacterial nor viral problems common to Hardy Geraniums have been observed on plants of the new Hardy Geranium under commercial conditions.

It is claimed:

1. A new and distinct cultivar of *Geranium maculatum* plant named 'Elizabeth Ann', as illustrated and described.

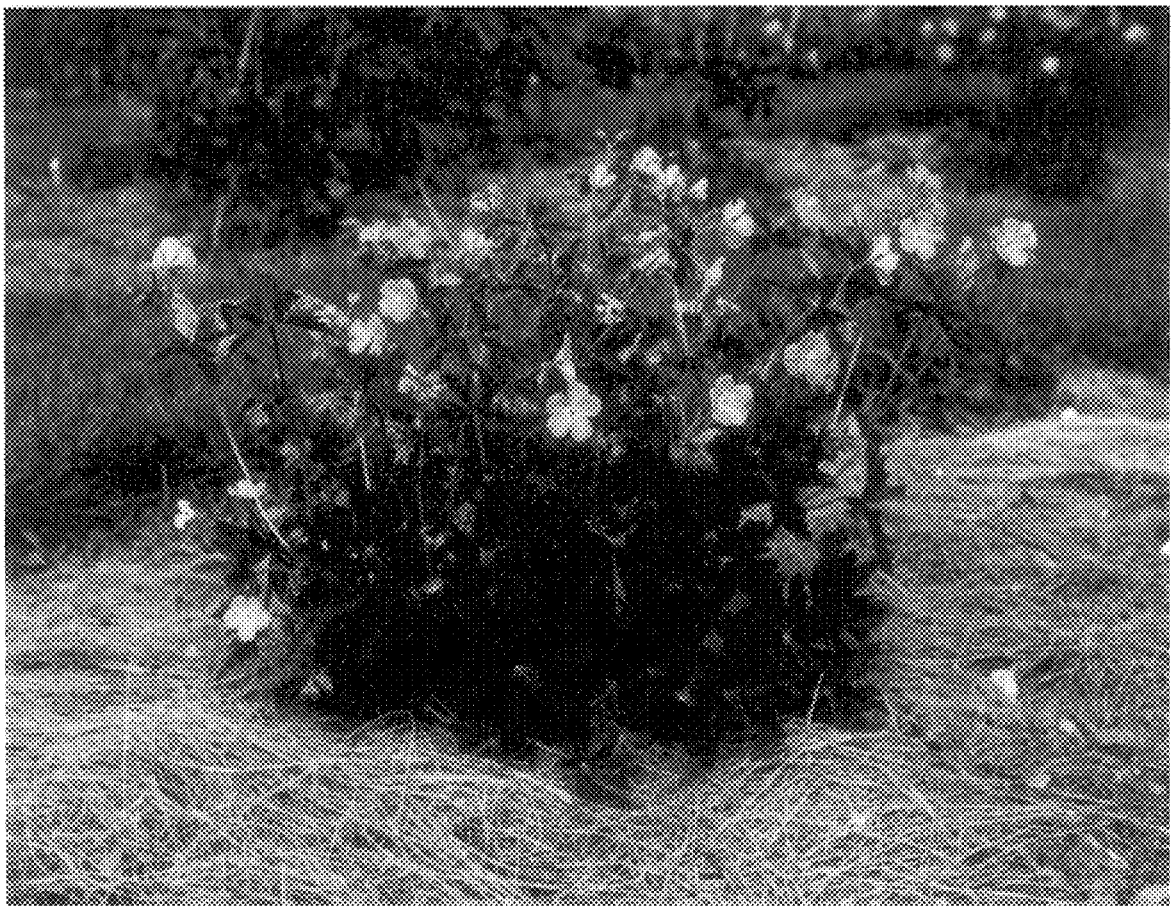

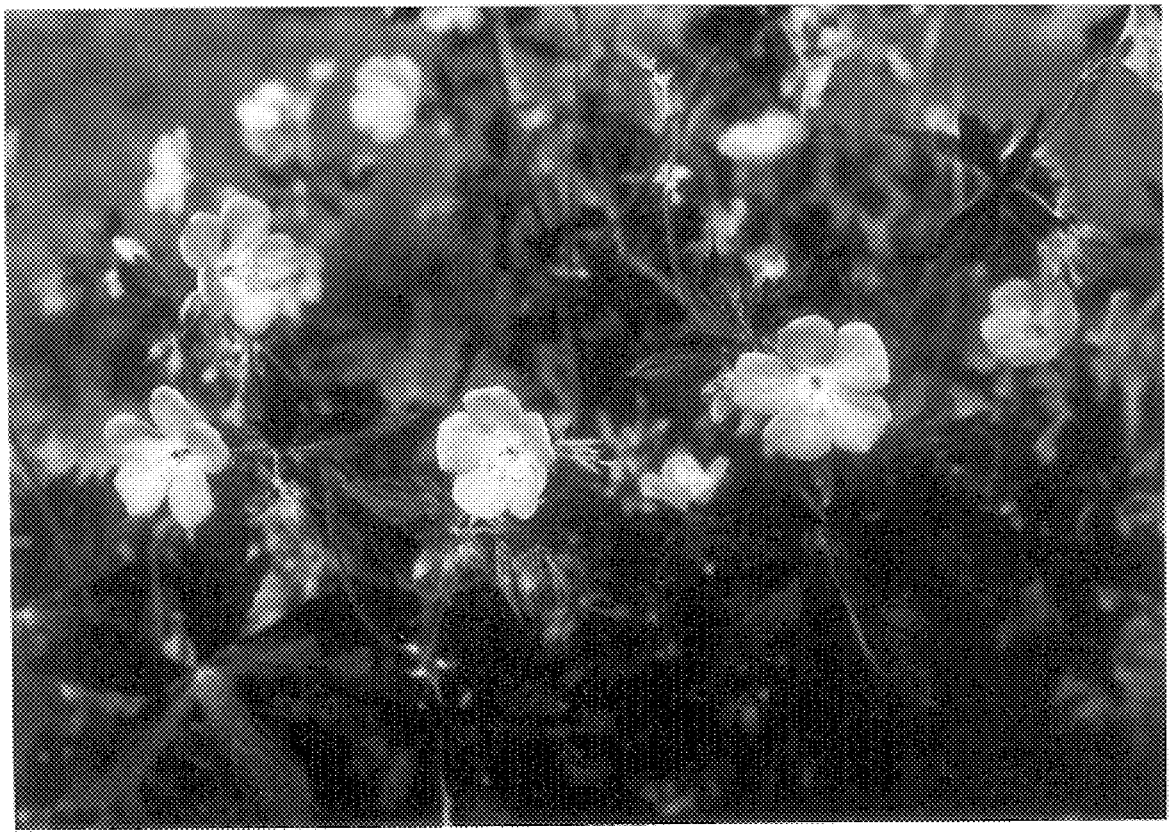
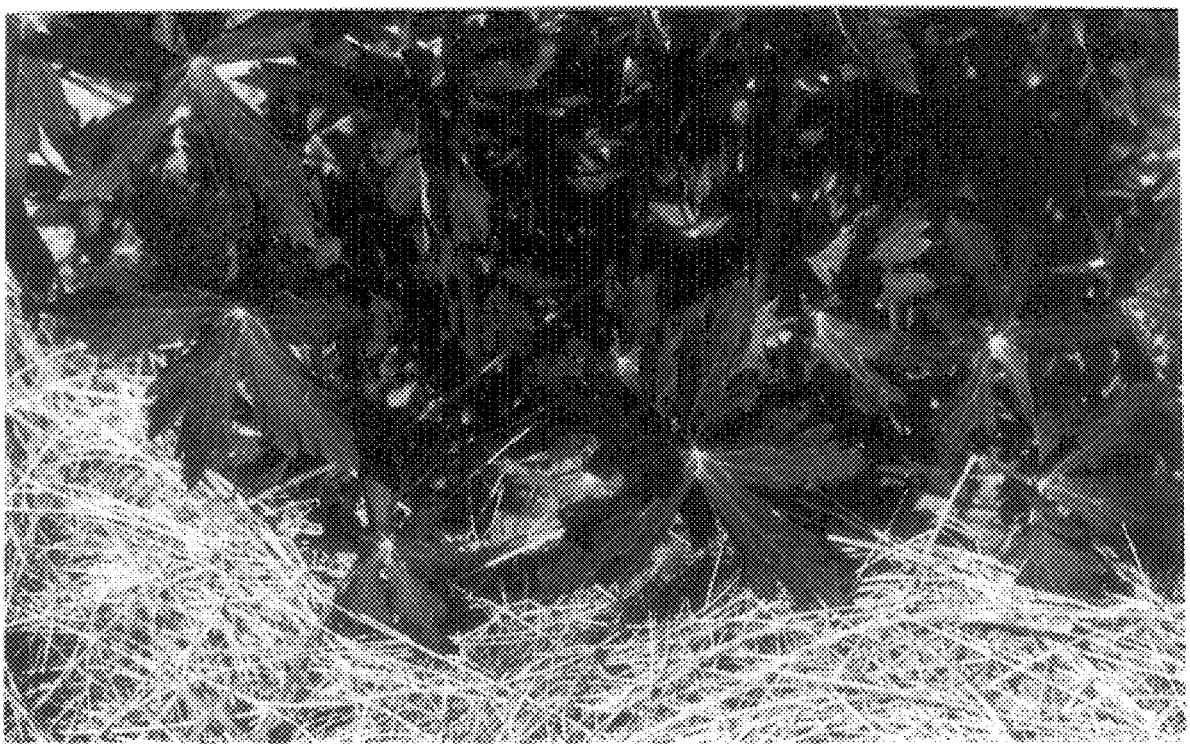

* * * * *